United States Patent
Hiramoto et al.

(10) Patent No.: US 10,619,179 B2
(45) Date of Patent: Apr. 14, 2020

(54) ELECTROCHEMICAL MEASURING METHOD AND ELECTROCHEMICAL MEASURING DEVICE

(71) Applicant: Panasonic Intellectual Property Management Co., Ltd., Osaka (JP)

(72) Inventors: Kaoru Hiramoto, Osaka (JP); Masahiro Yasumi, Osaka (JP); Hiroshi Ushio, Osaka (JP); Atsushi Shunori, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 181 days.

(21) Appl. No.: 15/329,293

(22) PCT Filed: Sep. 17, 2015

(86) PCT No.: PCT/JP2015/004752
§ 371 (c)(1),
(2) Date: Jan. 26, 2017

(87) PCT Pub. No.: WO2016/047114
PCT Pub. Date: Mar. 31, 2016

(65) Prior Publication Data
US 2017/0218423 A1 Aug. 3, 2017

Related U.S. Application Data

(60) Provisional application No. 62/055,185, filed on Sep. 25, 2014.

(30) Foreign Application Priority Data

Mar. 27, 2015 (JP) ................. 2015-065869

(51) Int. Cl.
*C12Q 1/02* (2006.01)
*G01N 27/416* (2006.01)
*G01N 33/483* (2006.01)
*C12M 1/34* (2006.01)
*C12M 1/42* (2006.01)

(52) U.S. Cl.
CPC .............. *C12Q 1/02* (2013.01); *G01N 27/416* (2013.01); *G01N 33/4833* (2013.01); *C12M 1/34* (2013.01); *C12M 1/42* (2013.01)

(58) Field of Classification Search
CPC .... C12Q 1/02; G01N 33/4833; G01N 27/416; C12M 1/34; C12M 1/42
See application file for complete search history.

(56) References Cited

U.S. PATENT DOCUMENTS 7,462,512 B2 * 12/2008 Levon ................ G01N 27/4148
438/123
2007/0087436 A1 4/2007 Miyawaki et al.

FOREIGN PATENT DOCUMENTS

WO 2004/092369 10/2004
WO 2010/055942 5/2010

OTHER PUBLICATIONS

The Extended European Search Report dated Sep. 4, 2017 for the related European Patent Application No. 15845383.7.
Michaela Nebel et al: "Microelectrochemical visualization of oxygen consumption of single living cells", Faraday Discussions, vol. 164, Jan. 1, 2013 (Jan. 1, 2013), p. 19, XP055400278.
International Search Report of PCT application No. PCT/JP2015/004752 dated Dec. 15, 2015.

* cited by examiner

Primary Examiner — Teresa E Knight
(74) Attorney, Agent, or Firm — McDermott Will & Emery LLP

(57) ABSTRACT

An electrochemical measuring method uses an electrochemical measuring device in which a measuring liquid is filled into a well. The electrochemical measuring method includes: a step of applying a measuring voltage to a working electrode and measuring a value of a first current flowing in the working electrode; a step of applying a non-measuring voltage to the working electrode; a step of introducing the biological sample into a container; and a step of applying the measuring voltage to the working electrode and measuring a value of a second current flowing in the working electrode.

16 Claims, 14 Drawing Sheets

ELECTROCHEMICAL MEASURING METHOD AND ELECTROCHEMICAL MEASURING DEVICE

This application is a U.S. national stage application of the PCT International Application No. PCT/JP2015/004752 filed on Sep. 17, 2015, which claims the benefit of foreign priority of Japanese patent application 2015-065869 filed on Mar. 27, 2015 and U.S. patent application 62/055,185 filed on Sep. 25, 2014, the contents all of which are incorporated herein by reference.

TECHNICAL FIELD

The present disclosure relates to an electrochemical measuring method and an electrochemical measuring apparatus for measuring and analyzing an activity state of a cell, tissue, or the like.

BACKGROUND ART

Cells and tissue are active in transporting and consuming various substances. For example, an embryo undergoes cell division while it consumes oxygen in the vicinity of the embryo. Accordingly, measurement of an environment in the vicinity of a sample such as a cell and tissue makes it possible to analyze an activity state of the sample.

Examples of methods for measuring the environment in the vicinity of a sample include a method for carrying out electrochemical measurement of a solution including the sample, using an electrochemical measuring device provided with a working electrode.

Note here that information on prior art documents relating to this application include, for example, PTL 1.

CITATION LIST

Patent Literature

PTL 1: International Publication WO2010/055942

SUMMARY OF THE INVENTION

An electrochemical measuring method of the present disclosure is a method for measuring a biological sample, using an electrochemical measuring device. The electrochemical measuring device includes a well, and a working electrode provided at the well, and a measuring liquid is filled into the well such that the measuring liquid is in contact with the working electrode.

The electrochemical measuring method includes the steps of: applying a measuring voltage to the working electrode, and measuring a value of a first current flowing in the working electrode; then applying a non-measuring voltage to the working electrode; then introducing the biological sample into the well; and then applying the measuring voltage to the working electrode, and measuring a value of a second current flowing in the working electrode.

Furthermore, an electrochemical measuring apparatus of the present disclosure is an electrochemical measuring apparatus for measuring a biological sample, using an electrochemical measuring device including a well and a working electrode provided at the well.

The electrochemical measuring apparatus includes a mounting portion on which the electrochemical measuring device is to be mounted, a terminal electrically connected to the working electrode of the electrochemical measuring device, and a control unit for controlling a voltage to be applied to the working electrode.

The control unit applies a measuring voltage to the working electrode and measures a value of a first current flowing in the working electrode before the biological sample is introduced, then applies a non-measuring voltage to the working electrode, then applies the measuring voltage to the working electrode and measures a value of a second current flowing in the working electrode after the biological sample is introduced into the electrochemical measuring device.

DESCRIPTION OF EMBODIMENTS

Figure 1:
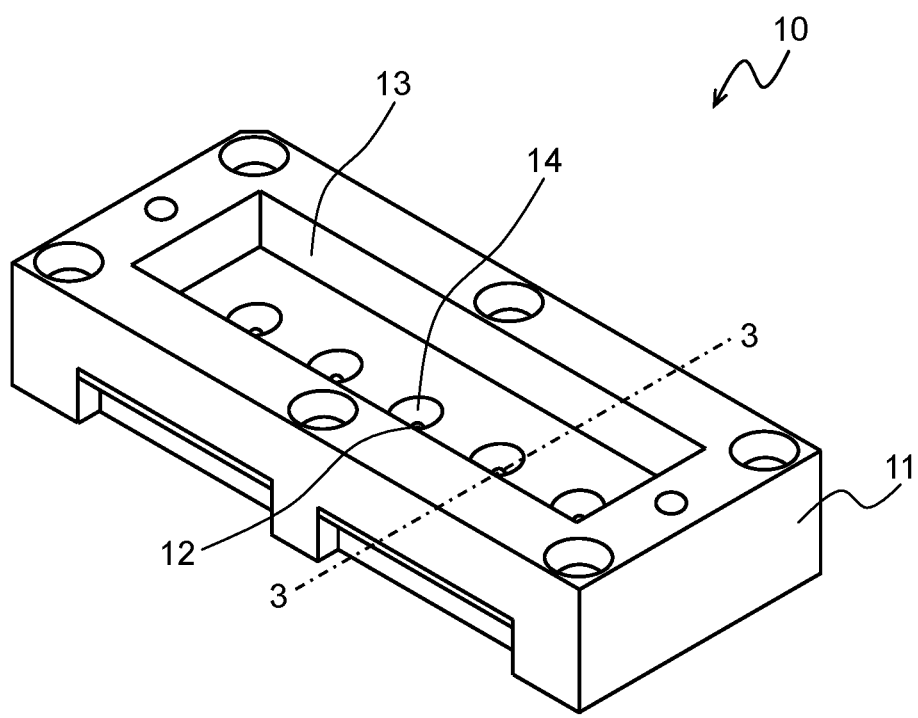
FIG. 1 is a perspective view of an electrochemical measuring device in accordance with a first exemplary embodiment.

In conventional electrochemical measurement, introduction or recovery of a biological sample is carried out with a measuring voltage applied. Consequently, current noise accompanying the introduction or recovery of the biological sample flows in a working electrode. The generated current noise may prevent accurate electrochemical measurement.

Hereinafter, an electrochemical measuring method and an electrochemical measuring apparatus in accordance with an exemplary embodiment of the present disclosure are described in detail. Note here that the following exemplary embodiments represent preferred specific examples of the present disclosure. Therefore, numerical values, shapes, materials, constituents, positions of the constituents, and connection forms, mentioned in the following exemplary embodiments, are merely exemplary, and not intended to limit the present disclosure. The constituents described in the following embodiments but not set forth in independent claims representing the most superordinate concept of the present disclosure are to be construed as optional constituents.

Furthermore, drawings are schematically shown, and are not necessarily strictly shown. In the drawings, the same references are given to substantially the same structures, and the overlapped description may be omitted or simplified.

First Exemplary Embodiment

Figure 2:
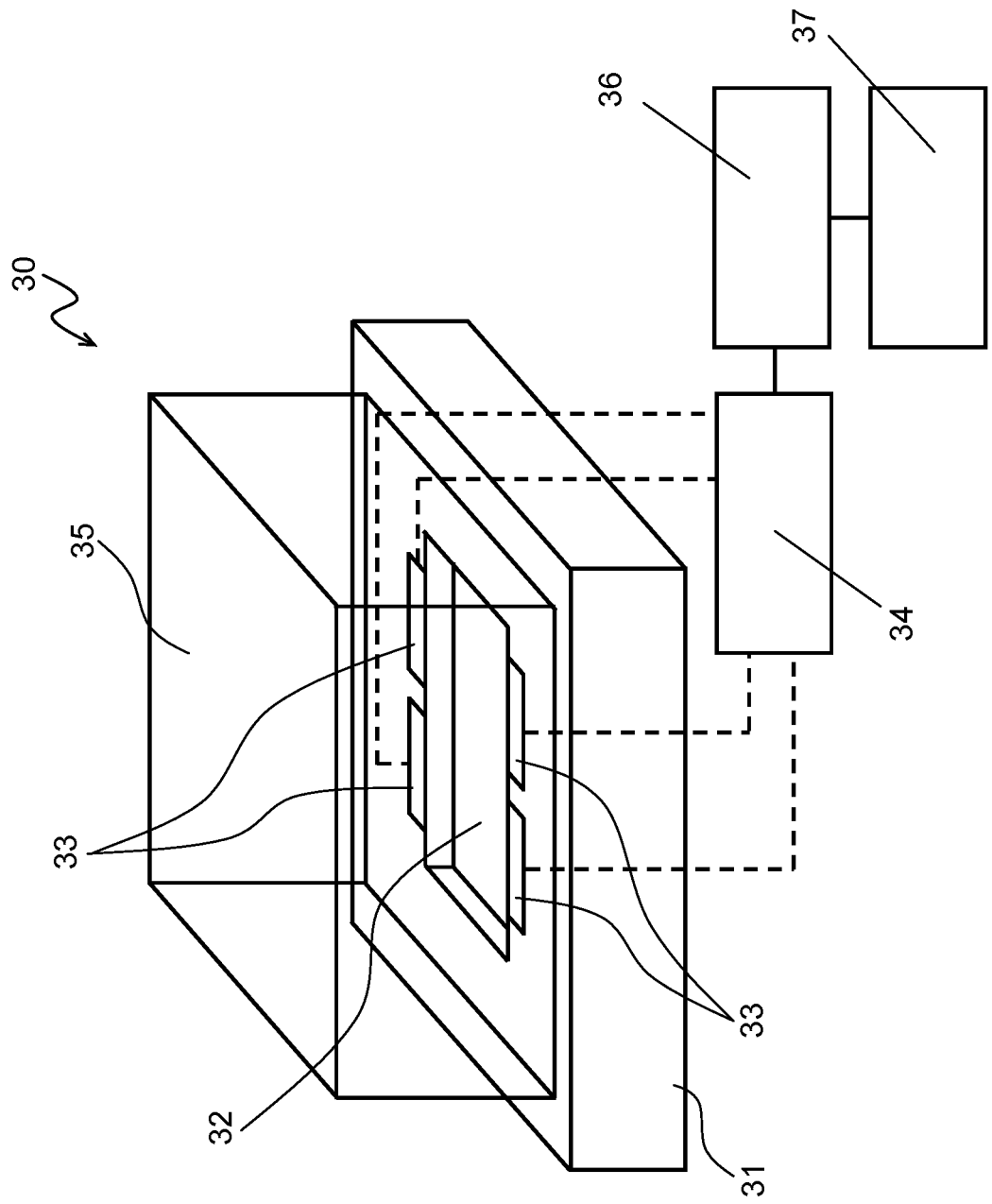
FIG. 2 is a perspective view of an electrochemical measuring apparatus in accordance with the first exemplary embodiment.
Figure 3:
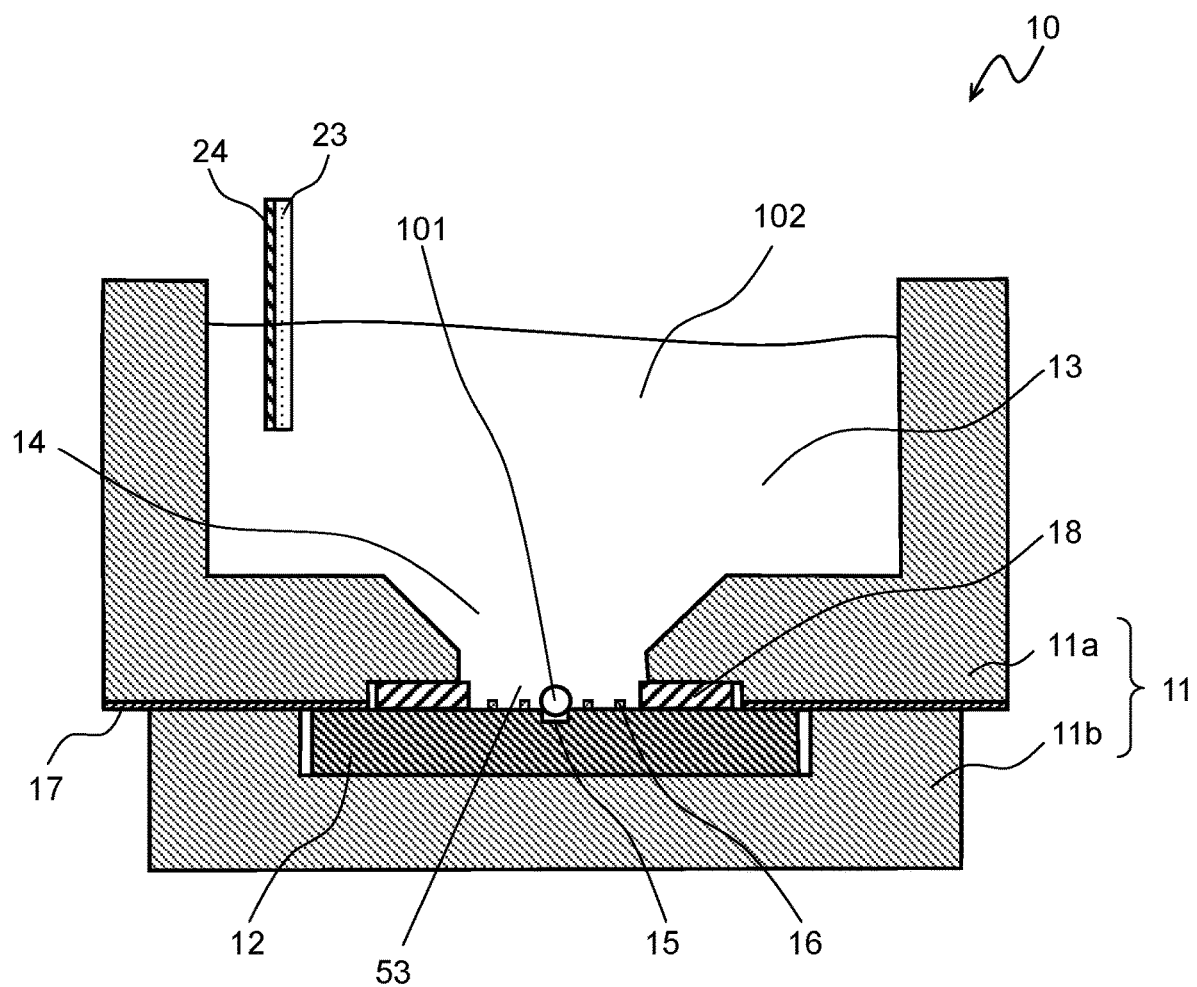
FIG. 3 is a schematic sectional view of the electrochemical measuring device in accordance with the first exemplary embodiment.
Figure 4:
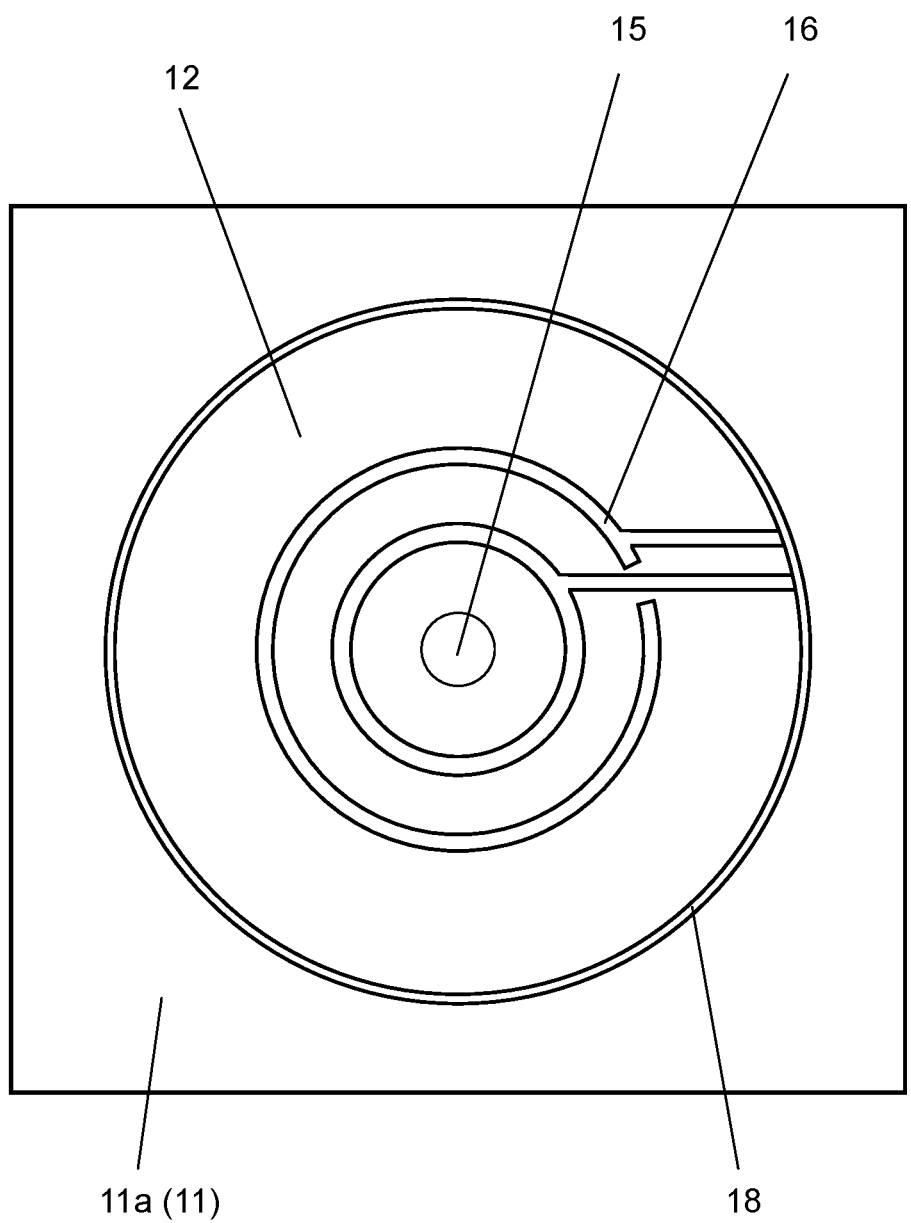
FIG. 4 is a schematic top view of the electrochemical measuring device in accordance with the first exemplary embodiment.

FIG. 1 is a perspective view of electrochemical measuring device 10 in accordance with this exemplary embodiment. FIG. 2 is a perspective view of electrochemical measuring apparatus 30 in accordance with this exemplary embodiment. FIG. 3 is a schematic sectional view of electrochemical measuring device 10 in accordance with this exemplary embodiment. FIG. 3 is a sectional view taken on line 3-3 of FIG. 1. FIG. 4 is a schematic top view of the electrochemical measuring device in accordance with this exemplary embodiment.

Electrochemical measuring device 10 is a device for measuring an activity state of biological sample 101, for example, a cell or tissue, such as an embryo.

Electrochemical measuring device 10 includes container 11 and electrode chip 12. Container 11 includes upper container 11a and lower container 11b.

Container 11 has electrode chip 12 packaged inside container 11. Container 11 includes reservoir portion 13 for holding measuring liquid 102. The bottom surface of reservoir portion 13 is provided with a plurality of inverted cone-shaped wells 14. Biological sample 101 is disposed in each well 14. Container 11 is produced by, for example, resin molding.

Electrode chip 12 has region 15 and working electrode 16. Region 15 is a place in which biological sample 101 is disposed. Working electrode 16 is used for electrochemical measurement of biological sample 101.

Region 15 is, for example, a recess portion provided at the upper surface of electrode chip 12. Note here that region 15 is not limited to a recess portion of electrode chip 12. For example, region 15 may be a part of a plane of electrode chip 12.

A plurality of working electrodes 16 surrounds the periphery of region 15. This configuration can keep a distance between biological sample 101 disposed in region 15 and working electrodes 16 constant.

Note here that a plurality of working electrodes 16 may be provided in such a manner that the distance from the center of region 15 to each of working electrodes 16 is different. Thus, electrochemical measuring device 10 can carry out electrochemical measurement at a plurality of positions whose distances from biological samples 101 are different.

In electrochemical measuring device 10, lower container 11b, electrode chip 12, and upper container 11a are sequentially stacked. Well 14 has through hole 53 on the bottom part thereof. Through hole 53 penetrates through the lower part of upper container 11a. With this configuration, working electrode 16 of electrode chip 12 is exposed at the bottom part of well 14.

The lower surface of a level difference portion at the periphery of container 11 is provided with connection terminal 17. Connection terminal 17 is electrically connected to working electrode 16. Connection terminal 17 is coupled to measuring instrument such as electrochemical measuring apparatus 30.

Sealing member 18 is provided between container 11 and electrode chip 12 in order to suppress leakage of measuring liquid 102.

Note here that working electrode 16 may be provided at region 15. Furthermore, connection terminal 17 may be formed in any place in container 11 as long as it is electrically connected to working electrode 16.

Furthermore, in electrochemical measuring device 10, the bottom surface of well 14 may not have through hole 53, and the bottom surface of well 14 may be closed. Region 15 and working electrode 16 may be provided not on electrode chip 12, but directly on the bottom surface of well 14 of container 11. In this case, electrode chip 12 is not required to be used.

Electrochemical measuring apparatus 30 carries out electrochemical measurement of a biological sample using electrochemical measuring device 10. Electrochemical measuring apparatus 30 carries out, for example, application of a voltage to working electrode 16 and measurement of a current flowing in working electrode 16.

Electrochemical measuring apparatus 30 includes stage 31, mounting portion 32, terminals 33, control unit 34, and cover 35.

Electrochemical measuring device 10 is mounted on mounting portion 32 on stage 31. Mounting portion 32 has, for example, a recess portion in the upper surface of stage 31. Electrochemical measuring device 10 is fixed to the recess portion of mounting portion 32.

Stage 31 is provided with terminals 33. Terminals 33 are brought into contact with connection terminal 17 of electrochemical measuring device 10. Thus, working electrode 16 is electrically connected to terminals 33. Furthermore, terminals 33 are electrically connected to control unit 34.

Control unit 34 controls magnitude of a voltage applied to the working electrode and timing at which the voltage is applied. Control unit 34 includes a power circuit, a voltage-applying circuit, and the like. Thus, control unit 34 can generate a command signal to apply a voltage and can apply a voltage to the working electrode.

Furthermore, electrochemical measuring apparatus 30 may include measurement unit 36 and operation unit 37. Measurement unit 36 measures, for example, a current flowing in working electrode 16 by the applied voltage. Operation unit 37 calculates, for example, an activity degree of biological sample 101 based on the measured current value.

As shown in FIG. 2, control unit 34, measurement unit 36, and operation unit 37 may be configured by independent circuits, respectively. Alternatively, control unit 34, measurement unit 36, and operation unit 37 may be configured by one integrated circuit (IC).

Cover 35 is provided in order to keep a measurement environment of biological sample 101 appropriate. In other words, cover 35 forms a measurement environment isolated from the outside air. Providing cover 35 allows electrochemical measuring apparatus 30 to measure biological sample 101 in an appropriate environment.

Cover 35 is provided above stage 31. Electrochemical measuring device 10 mounted on mounting portion 32 is completely covered with cover 35.

Herein, the appropriate environment for measurement of biological sample 101 is, for example, an environment in which the temperature is 37° C. and 5% carbon dioxide is contained in the air. In order to maintain this environment, electrochemical measuring apparatus 30 may be provided with a supply port for supplying carbon dioxide, a temperature sensor, a heater, and the like.

Hereinafter, with reference to FIGS. 3 and 4, an operation of electrochemical measuring device 10 when biological sample 101 is measured is described.

Biological sample 101 is, for example, an embryo. The embryo includes undifferentiated and cleavage fertilized eggs.

An embryo undergoes division while it consumes the surrounding oxygen inside the follicle. Electrochemical measuring apparatus 30 can measure the amount of oxygen dissolved in the vicinity of an embryo by the use of working electrode 16. Then, an activity state of oxygen consumption by the embryo can be assessed based on the measured amount of oxygen.

Reservoir portion 13 is provided with reference electrode 23 and counter electrode 24.

Measuring liquid 102 is filled into reservoir portion 13 and well 14 such that measuring liquid 102 is in contact with working electrode 16, reference electrode 23, and counter electrode 24.

Working electrode 16, reference electrode 23, and counter electrode 24 are electrically connected to electrochemical measuring apparatus 30.

Control unit 34 and measurement unit 36 of electrochemical measuring apparatus 30 are, for example, a potentiostat. The potentiostat is an instrument for making electric potential of working electrode 16 with respect to reference electrode 23 constant.

Biological sample 101 is disposed in region 15 formed in the upper surface of electrode chip 12.

When the amount of oxygen dissolved in the vicinity of biological sample 101 is measured, oxygen-reduction potential is applied to working electrode 16 by the use of a potentiostat. Thus, oxygen dissolved in the vicinity of working electrode 16 is reduced. Reduction of oxygen allows a current to flow in working electrode 16. The current flowing in working electrode 16 is measured by the potentiostat.

A value of a current flowing in working electrode 16 is correlated with the amount of oxygen dissolved in the vicinity of working electrode 16. Therefore, measurement of the value of a current in working electrode 16 disposed in the vicinity of biological sample 101 permits estimation of a dissolved oxygen concentration (an amount of dissolved oxygen) as the substance concentration in the vicinity of biological sample 101.

Note here that counter electrode 24 may not be provided. That is to say, reference electrode 23 may have a function as counter electrode 24 in addition to the function as reference electrode 23.

Figure 5:
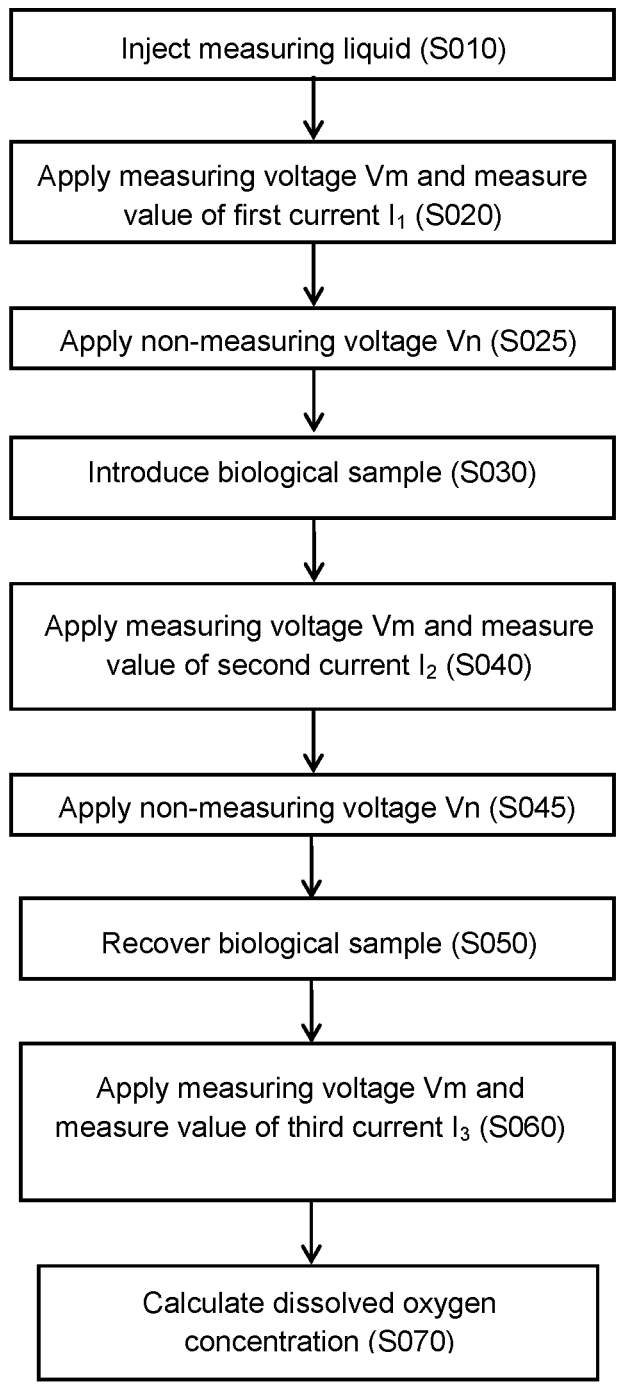
FIG. 5 is a flowchart showing an electrochemical measuring method in accordance with the first exemplary embodiment.
Figure 6:
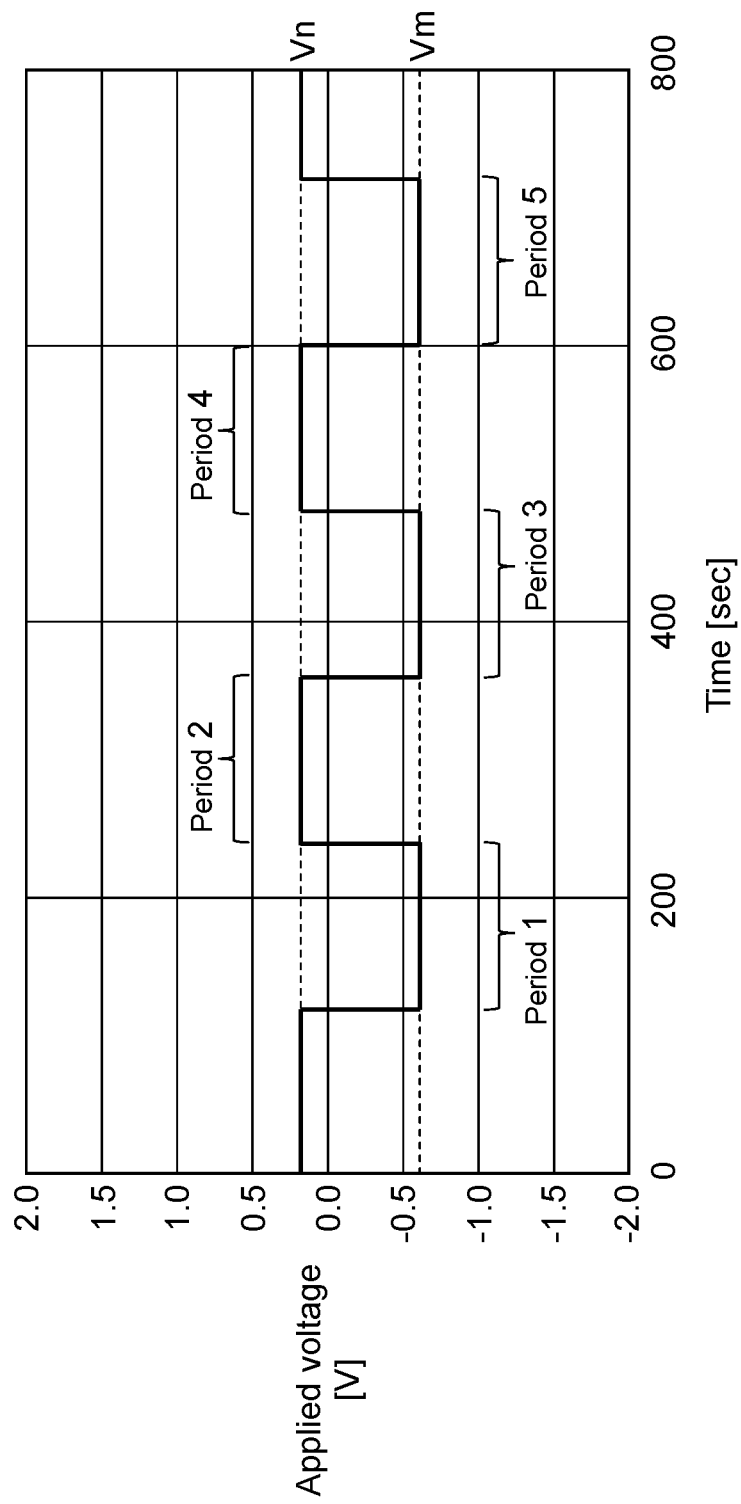
FIG. 6 is a graph showing a voltage application protocol in accordance with the first exemplary embodiment.

FIG. 5 is a flowchart showing an electrochemical measuring method in accordance with this exemplary embodiment. FIG. 6 shows a voltage application protocol showing one example of application timing of a voltage to be applied to working electrode 16.

Hereinafter, with reference to FIGS. 5 and 6, an electrochemical measuring method for measuring an oxygen consumption by single biological sample 101 such as an embryo is described. Herein, single biological sample 101 is one cell, one cell aggregation, and one tissue. The single biological sample 101 does not include a plurality of cells contained in a state in which they are distributed in measuring liquid 102.

A plurality of working electrodes 16 is provided on the upper surface of electrode chip 12. Working electrodes 16 are disposed at different distances from the center of region 15, respectively.

The electrochemical measuring method in accordance with this exemplary embodiment includes a step of injecting measuring liquid 102 into container 11 (S010); a step of applying measuring voltage Vm to working electrode 16 and measuring a value of first current $I_1$ in a blank state before biological sample 101 is introduced (S020); a step of applying non-measuring voltage Vn to working electrode 16 (S025); a step of introducing biological sample 101 (S030); a step of applying measuring voltage Vm to working electrode 16 and measuring a value of second current $I_2$ after biological sample 101 is introduced (S040); a step of applying non-measuring voltage Vn to working electrode 16 (S045); a step of recovering biological sample 101 (S050); a step of applying measuring voltage Vm to working electrode 16, and measuring a value of third current $I_3$ in a blank state after biological sample 101 is recovered (S060); and a step of calculating a dissolved oxygen concentration (an amount of dissolved oxygen) as a substance concentration in measuring liquid 102 from the measured current values $I_1$, $I_2$, and $I_3$ (S070). From a change of the concentration of the dissolved oxygen, activity of biological sample 101 is measured.

In step S010, measuring liquid 102 is injected into reservoir portion 13 and well 14 of container 11. Measuring liquid 102 is in contact with working electrode 16, reference electrode 23, and counter electrode 24. Then, electrochemical measuring device 10 is mounted on mounting portion 32 of electrochemical measuring apparatus 30. At this time, connection terminal 17 is in contact with terminal 33. In this Example, working electrode 16 and counter electrode 24 are described using a platinum electrode. Furthermore, reference electrode 23 is described using a silver-silver chloride electrode. However, the electrode material is not limited to these materials.

Herein, when container 11 is previously filled with measuring liquid 102, procedure may be started from step S020.

In step S020, measuring voltage Vm is applied to working electrode 16, and a value of first current $I_1$ before biological sample 101 is introduced is measured. Measuring voltage Vm is applied in period 1 shown in FIG. 6. Measuring voltage Vm is at oxygen-reduction potential. In this exemplary embodiment, measuring voltage Vm is, for example, −0.6 V. Furthermore, period 1 is a period from 120th second to 240th second. Period 1 is preferably 10 seconds or more and 120 seconds or less. Note here that for the purpose of shortening the measurement time of the electrochemical measurement, period 1 may be 5 seconds or more and 10 seconds or less. In a period before period 1, non-measuring voltage Vn is applied. Herein, measuring voltage Vm is a voltage to be applied at the time of measurement. Non-measuring voltage Vn is a voltage to be applied so as to prevent a current from flowing in the electrode.

Applying of measuring voltage Vm to working electrode 16 allows dissolved oxygen in the vicinity of working electrode 16 to be reduced, and thus allows oxygen-reduction current to flow in working electrode 16. Measurement unit 36 measures a value of first current $I_1$ flowing in working electrode 16.

In this way, in step S020, it is possible to measure the value of first current $I_1$ resulting from the dissolved oxygen concentration (the amount of dissolved oxygen) included in measuring liquid 102 in a blank state, which is not influenced by biological sample 101.

In step S025, non-measuring voltage Vn is applied to working electrode 16. Then, in step S030, biological sample 101 is introduced. Non-measuring voltage Vn is applied in period 2 shown in FIG. 6. Non-measuring voltage Vn is an open-circuit voltage of electrochemical measuring apparatus 30. In this exemplary embodiment, non-measuring voltage Vn is, for example, 0.2 V. Furthermore, period 2 is a period from 240th second to 360th second. Period 2 is preferably 30 seconds or more and 120 seconds or less.

Biological sample 101 is disposed in region 15 with non-measuring voltage Vn applied to working electrode 16. In region 15, one biological sample 101 is disposed. Since a current does not flow in working electrode 16, it is possible to suppress current noise when biological sample 101 is disposed in region 15.

Furthermore, even when biological sample 101 is brought into contact with working electrode 16, since a current does not flow to biological sample 101, it is possible to prevent biological sample 101 from being damaged.

In step S040, a value of second current $I_2$ after biological sample 101 is introduced is measured.

Measuring voltage Vm is applied in period 3 shown in FIG. 6. Measuring voltage Vm is at oxygen-reduction potential. In this exemplary embodiment, measuring voltage Vm is, for example, −0.6 V. Furthermore, period 3 is a period from 360th second to 480th second. Period 3 is preferably 10 seconds or more and 120 seconds or less. Note here that for the purpose of shortening the measurement time in the electrochemical measurement, period 3 may be 5 seconds or more and 10 seconds or less.

In this way, in step S040, it is possible to measure a value of second current $I_2$ resulting from the dissolved oxygen concentration (the amount of dissolved oxygen), which is influenced by respiration activity of biological sample 101.

Biological sample 101 disposed in region 15 consumes the dissolved oxygen in the vicinity in measuring liquid 102 with the respiration activity. Consequently, in the vicinity of biological sample 101 in measuring liquid 102, oxygen decreases. Furthermore, the dissolved oxygen in measuring liquid 102 is nearer to an oxygen saturation state of measuring liquid 102 as a distance from biological sample 101 increases.

As the respiration activity of biological sample 101 is more active, a larger amount of oxygen is consumed in the vicinity of biological sample 101. That is to say, the size of the oxygen concentration gradient in the vicinity of biological sample 101 is determined by the amount of respiration activity of a fertilized egg as biological sample 101.

In step S045, non-measuring voltage Vn is applied to working electrode 16. In step S050, biological sample 101 is recovered. Non-measuring voltage Vn is applied in period 4 shown in FIG. 6. Non-measuring voltage Vn is an open-circuit voltage of entire electrochemical measuring apparatus 30 including a measuring instrument coupled to electrochemical measuring device 10. At this time, electrochemical measuring device 10 is filled with measuring liquid 102. In this exemplary embodiment, non-measuring voltage Vn is, for example, 0.2 V. Furthermore, period 4 is a period from 480th second to 600th second. Period 4 is preferably 30 seconds or more and 120 seconds or less.

Biological sample 101 is taken out from measuring liquid 102 with non-measuring voltage Vn applied to working electrode 16. At this time, since a current does not flow in working electrode 16, it is possible to suppress current noise when biological sample 101 is taken out.

Furthermore, even when biological sample 101 is brought into contact with working electrode 16, since current does not flow in biological sample 101, biological sample 101 can be prevented from being damaged.

In step S060, measuring voltage Vm is applied to working electrode 16 and a value of third current $I_3$ after biological sample 101 is recovered is measured. Measuring voltage Vm is applied in period 5 shown in FIG. 6. Measuring voltage Vm is at oxygen-reduction potential. In this exemplary embodiment, measuring voltage Vm is, for example, −0.6 V. Furthermore, period 5 is a period from 600th second to 720th second. Period 5 is preferably 10 seconds or more and 120 seconds or less. Note here that for the purpose of shortening the measurement time of the electrochemical measurement, period 5 may be 5 seconds or more and 10 seconds or less.

Applying of measuring voltage Vm to working electrode 16 allows the dissolved oxygen in the vicinity of working electrode 16 to be reduced, and therefore allows oxygen-reduction current to flow in working electrode 16. Measurement unit 36 measures a value of third first current $I_3$ flowing in working electrode 16.

In this way, in step S060, it is possible to measure a value of third current $I_3$ resulting from the dissolved oxygen concentration contained in measuring liquid 102 in a blank state, which is not directly influenced by biological sample 101.

Note here that it is preferable that measuring voltages Vm in step S020, step S040 and step S060 are the same value. Furthermore, it is preferable that non-measuring voltages Vn in step S030 and step S050 are the same value.

Furthermore, it is preferable that period 1, period 3 and period 5 have the same time. Furthermore, it is preferable that period 2 and period 4 have the same time.

In step S070, the dissolved oxygen concentration (the amount of dissolved oxygen) is calculated from the measured values of first current $I_1$, second current $I_2$, and third current $I_3$.

Hereinafter, a method for calculating the dissolved oxygen concentration in the vicinity of biological sample 101 in step S040 using the value of second current $I_2$ measured in step S040 is described.

Firstly, as shown in Mathematical formula (1), current change rate $I^*_2$ of each working electrode 16 is calculated by dividing the value of second current $I_2$ of each working electrode 16 by the value of first current $I_1$ measured in each working electrode 16.

[Math. 1]

$$I^*_2 = I_2/I_1 \qquad \text{(Math. 1)}$$

In this way, even when absolute values of first current $I_1$ and second current $I_2$ flowing in a plurality of working electrodes 16 are different from each other, they can be normalized as current change rate $I^*_2$.

As mentioned above, in step S040, as biological sample 101 consumes oxygen, the concentration of the dissolved oxygen becomes low in the vicinity of biological sample 101. Furthermore, as the distance from biological sample 101 increases, the influence of biological sample 101 on the dissolved oxygen in measuring liquid 102 decreases.

Therefore, in step S040, the current change rate $I^*_2$ of working electrode 16 in the vicinity of biological sample 101 increases. Furthermore, as the distance from biological sample 101 increases, the current change rate $I^*_2$ of working electrode 16 decreases.

The current change rate $I^*_2$ in each working electrode 16 is in reverse proportion to the distance from biological sample 101 in each working electrode 16.

Therefore, the slope of a straight line obtained by plotting the current change rate $I*_2$ in each working electrode 16 with respect to the inverse of the distance from biological sample 101 shows an oxygen concentration gradient formed corresponding to the consumption of oxygen by biological sample 101.

The oxygen concentration gradient formed corresponding to the consumption of oxygen by biological sample 101 is denoted by the following mathematical formula Math. 2.

[Math. 2]

$$\Delta C = C_0 \times (I_1 - I_2)/I_1 \times R/r \quad \text{(Math. 2)}$$
$$= C_0 \times (1 - I_2^*) \times R/r$$

In the formula, $C_0$ represents a bulk concentration of dissolved oxygen. The bulk concentration of dissolved oxygen denotes a concentration of dissolved oxygen contained in measuring liquid 102 in a state in which biological sample 101 is not included. Furthermore, r represents a radius of biological sample 101. R represents a distance from the center of biological sample 101 to the center of working electrode 16. Note here that the center of biological sample 101 may be the center of region 15.

It is considered that in spherical biological sample 101 such as an embryo, the oxygen concentration gradient is formed in a spherical shape from the center of biological sample 101 by the respiration activity. Therefore, the total sum of oxygen fluxes to the surface of spherical biological sample 101 follows the Fick's first law and, therefore, is denoted by the following mathematical formula Math. 3.
[Math. 3]

$$F = 4\pi r D \Delta C \quad \text{(Math. 3)}$$

Herein, D is a diffusion coefficient of the dissolved oxygen in measuring liquid 102.

In this exemplary embodiment, since biological sample 101 is disposed in region 15, biological sample 101 is considered to be diffused hemispherically from the center of region 15. Therefore, the oxygen consumption by biological sample 101 in accordance with this exemplary embodiment is denoted by the following mathematical formula Math. 4.
[Math. 4]

$$F = 2\pi r D \Delta C \quad \text{(Math. 4)}$$

The concentration gradient of dissolved oxygen and the oxygen flux in step S020 and step S060 are also calculated in the same manner as mentioned above. That is to say, the concentration gradient of dissolved oxygen and the flux of oxygen in each step are calculated by using the values of first current $I_1$, second current $I_2$, and third current $I_3$. From the size of the flux of oxygen in step S040, the activity of biological sample 101 is measured.

Note here that actually, due to attached product or the like on the surface of working electrode 16, a value of oxygen-reduction current flowing in each working electrode 16 is decreased over time.

Furthermore, due to the influence of the convection inside well 14, even in a blank state, the oxygen flux may be formed inside well 14.

Therefore, in order to increase the accuracy of the amount of oxygen consumption by biological sample 101, the oxygen flux calculated in step S040 may be corrected by the oxygen flux in a blank state in step S020 and step S060.

Note here that the substance concentration to be calculated is not necessarily limited to the dissolved oxygen concentration. For example, the substance concentration may be a concentration of a substance showing activity of biological sample 101.

Furthermore, the electrochemical measurement of biological sample 101 may be carried out by a part of steps of the electrochemical measuring method in accordance with this exemplary embodiment. For example, only the values of the first and second currents may be measured, and the values of the second and third currents may be measured without measuring the value of the first current.

As mentioned above, in order to carry out a electrochemical measuring method of this Example, control unit 34 of electrochemical measuring apparatus 30 carries out a step of applying measuring voltage Vm to working electrode 16 and measuring a value of first current $I_1$ before biological sample 101 is introduced; a step of applying non-measuring voltage Vn to working electrode 16 at the timing before biological sample 101 is introduced into electrochemical measuring device 10; a step of applying measuring voltage Vm to working electrode 16 and measuring a value of second current $I_2$ after biological sample 101 is introduced; a step of applying non-measuring voltage Vn to working electrode 16 at the timing before biological sample 101 is recovered from electrochemical measuring device 10; and a step of applying measuring voltage to working electrode 16, and measuring a value of third current $I_3$ after recovering biological sample 101.

Modification Example 1

Figure 7:
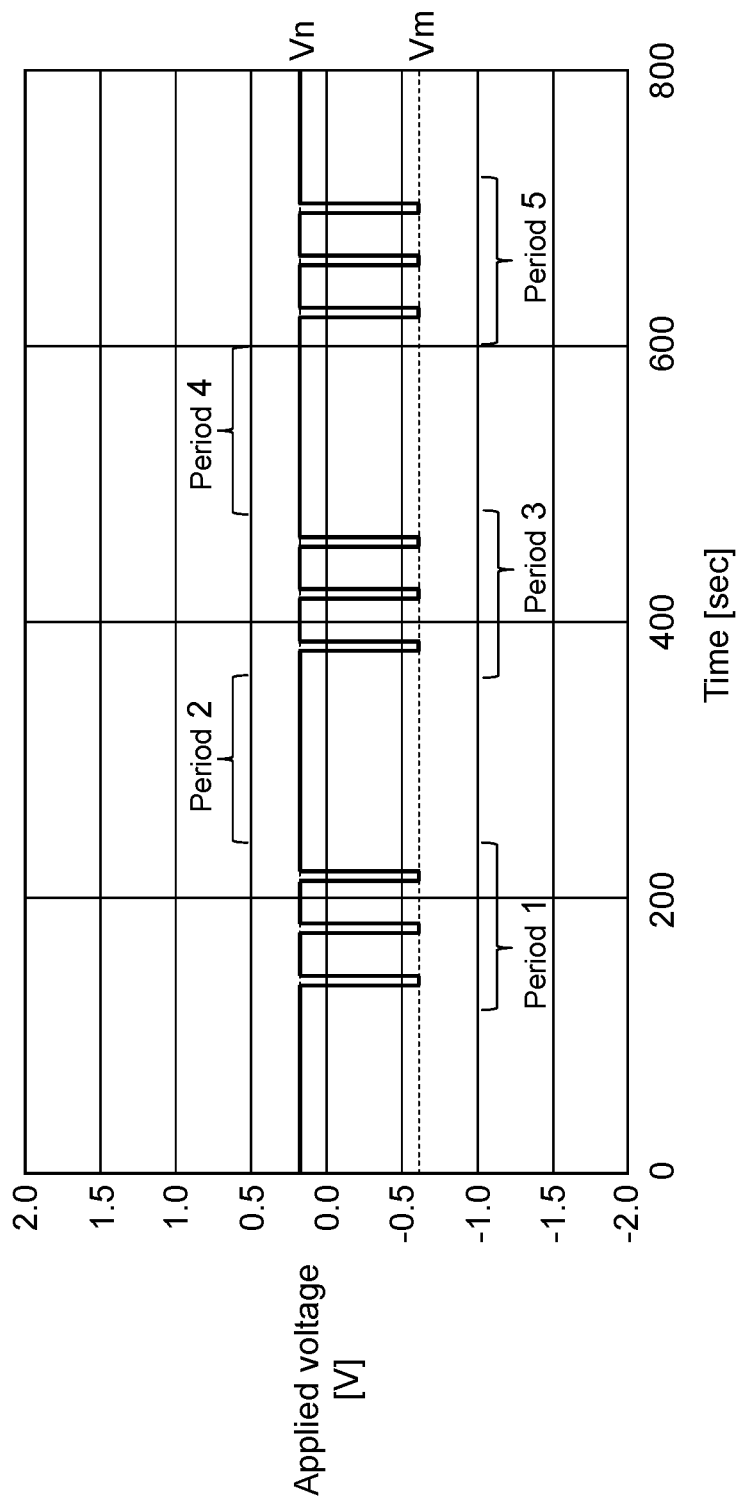
FIG. 7 is a graph showing a voltage application protocol in accordance with modification Example 1 of the first exemplary embodiment.

FIG. 7 is a graph showing a voltage application protocol in accordance with modification Example 1 of the first exemplary embodiment.

This modification example is different from the above-mentioned exemplary embodiment in the application method of measuring voltage Vm in periods 1, 3 and 5.

Hereinafter, this modification example is described.

In this modification example, measuring voltage Vm is applied in a pulse-like waveform. That is to say, for example, in period 1 of step S020, measuring voltage Vm and non-measuring voltage Vn are alternately applied to working electrode 16, repeatedly. The same is true in periods 3 and 5. In each period, application time of measuring voltage Vm in one pulse is preferably one second or more and 10 seconds or less. Furthermore, in each period, pulse waveform is given at least twice. In example shown in FIG. 7, in period 1, measuring voltage Vm is applied three times. The application time of measuring voltage Vm is 5 seconds.

Furthermore, the application time of non-measuring voltage Vn between measuring voltages Vm is one second or more and 25 seconds or less.

The application time of non-measuring voltage Vn may be equal to that of measuring electric potential Vm. For example, when the application time of measuring electric potential Vm is five seconds, the application time of non-measuring electric potential Vn may be five seconds.

Note here that it is preferable that the pulse waveforms of the voltages applied in periods 1, 3 and period 5 are equal to each other. That is to say, it is preferable that the pulse widths and time periods of voltage waveforms shown in FIG. 6 are equal to each other.

When a pulse-like voltage is applied, the waveform of a current to be measured also becomes a pulse-like waveform. At this time, for example, using a current value obtained in first pulse of period 1, the other current value may be normalized. Thus, the normalized oxygen-reduction current value can be obtained.

Applying of a pulse-like voltage can shorten integrated time of voltage application in a state in which biological sample 101 is disposed in region 15.

Shortening of the integrated time of the applied voltage can suppress accumulation of reduced product generated by reduction of oxygen on the surface of working electrode 16. Thus, it is possible to suppress the decrease over time of a value of current flowing in working electrode 16. Furthermore, it is possible to decrease the influence to be exerted on biological sample 101 by the reduced product.

Modification Example 2

Figure 8:
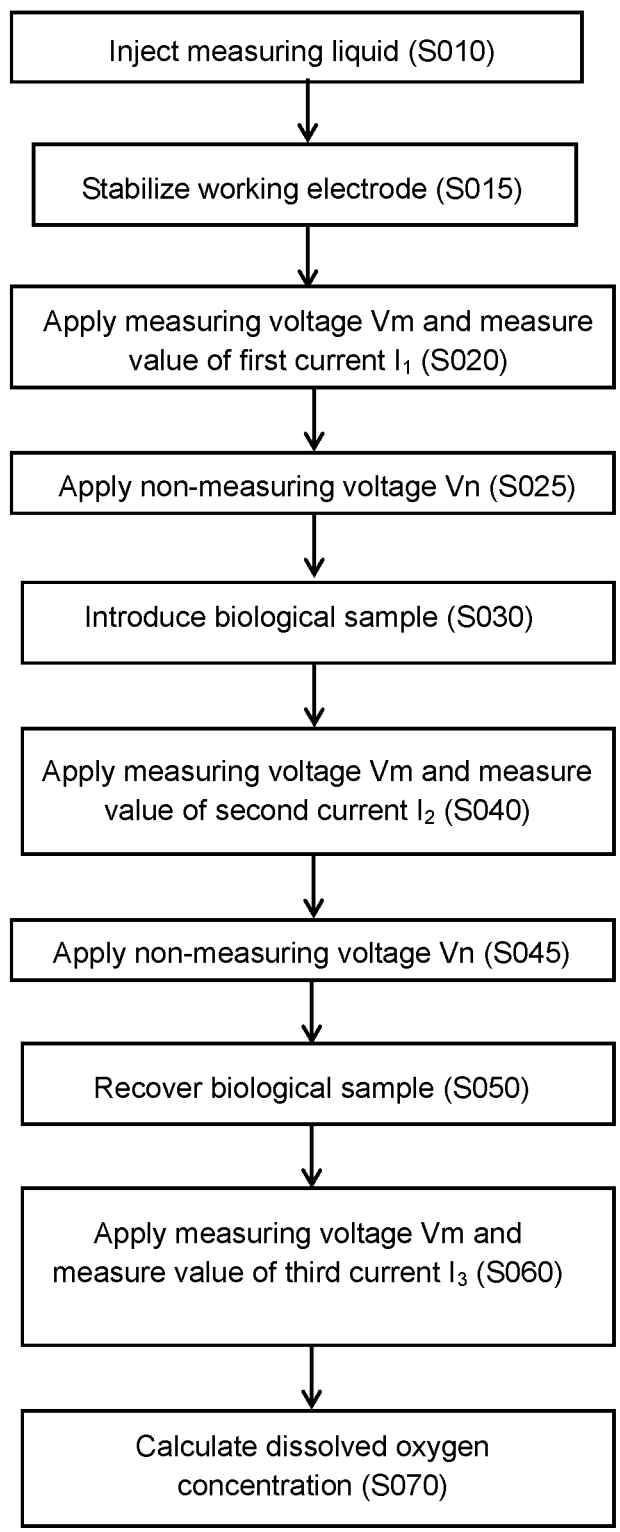
FIG. 8 is a flowchart showing an electrochemical measuring method in accordance with modification Example 2 of the first exemplary embodiment.
Figure 9:
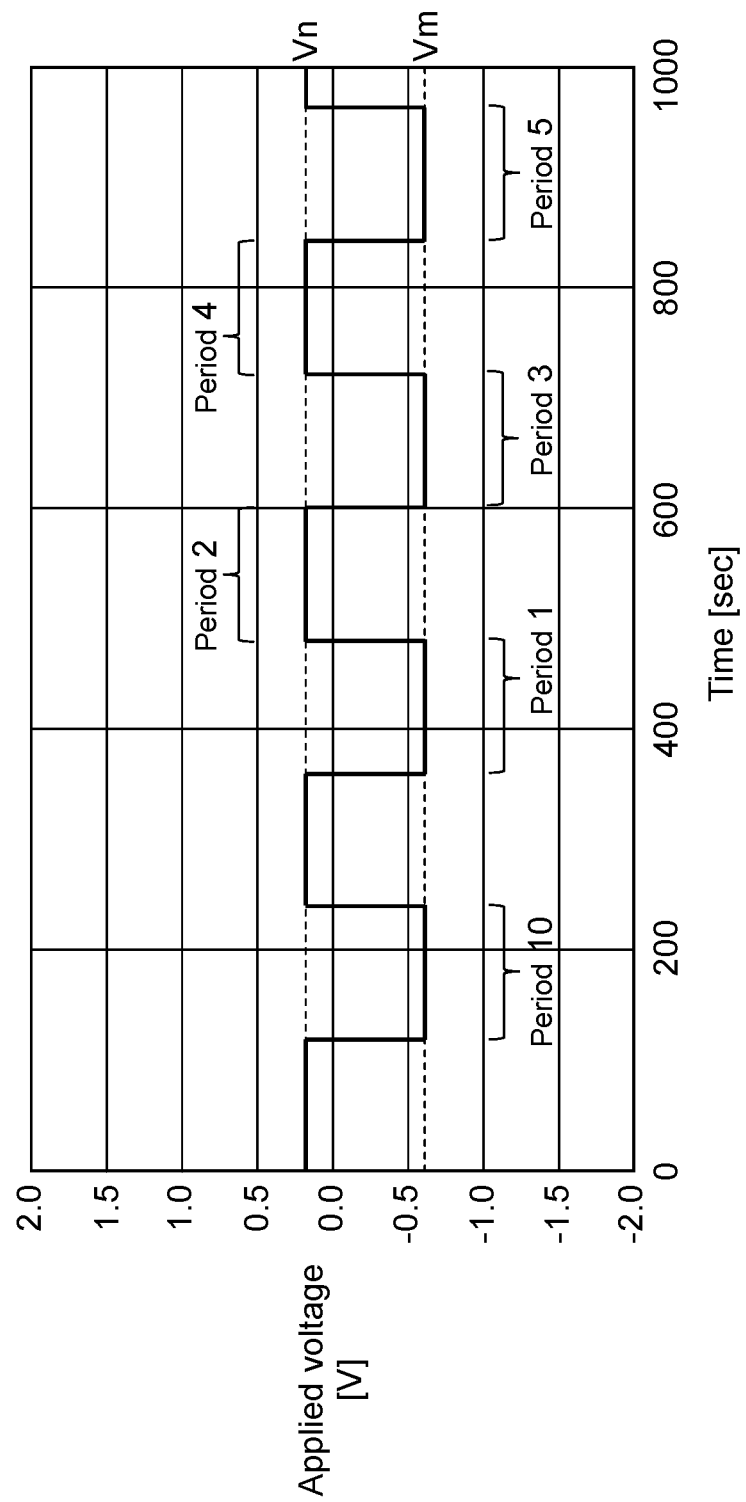
FIG. 9 is a graph showing a voltage application protocol in accordance with modification Example 2 of the first exemplary embodiment.

FIG. 8 is a flowchart showing an electrochemical measuring method in accordance with this modification example. FIG. 9 is a graph showing a voltage application protocol in accordance with modification Example 2 of this exemplary embodiment.

This modification example is different from the exemplary embodiment in that period 10 during which measuring voltage Vm is applied is further provided before period 1.

Hereinafter, this modification example is described.

The electrochemical measuring method of this modification example includes step S015 of stabilizing a value of current flowing in working electrode 16 before step S020 of measuring a value of first current $I_1$.

Step S015 is carried out after step S010 of injecting measuring liquid into container 11.

In step S015, measuring voltage Vm is applied to working electrode 16. Measuring voltage Vm is applied in period 10.

After step S015 is carried out, measurement later than step S020 is carried out sequentially.

Period 10 is time necessary for working electrode 16 to be stabilized. Furthermore, the application time of measuring voltage Vm may be determined while the value of a current flowing in working electrode 16 is monitored.

When a voltage is applied for the first time after a measuring liquid is injected into electrochemical measuring device 10, a large transient current may flow depending on a state of the measuring instrument or working electrode 16.

When measuring voltage Vm is applied in advance before the value of first current $I_1$ is measured in step S020, it is possible to decrease the influence of the transient current in measurement in step S020.

Furthermore, the value of a current flowing in working electrode 16 is stabilized when a voltage is applied to working electrode 16 for a while, so that the value of current is decreased to some extent. In this way, the state of working electrode 16 can be stabilized.

Therefore, by applying measuring voltage Vm to working electrode 16 in advance, it is possible to minimize current change of the value of first current $I_1$ measured in step S020.

Furthermore, providing step S015 allows abnormality of working electrode 16 and the measuring instrument to be detected before measurement in step S020. Then, when abnormality occurs, an error can be displayed on a display unit and the like (not shown) based on the oxygen-reduction current obtained in step S015. Note here that measuring voltage Vm applied to working electrode 16 in step S015 may be a constant voltage or may be a pulse-like voltage.

Second Exemplary Embodiment

Hereinafter, an electrochemical measuring method of biological sample 101 in accordance with this exemplary embodiment is described with reference to drawings. Note here that in this exemplary embodiment, the same reference numerals are given to the same configuration as in the first exemplary embodiment, and detailed description thereof is omitted.

Figure 10:
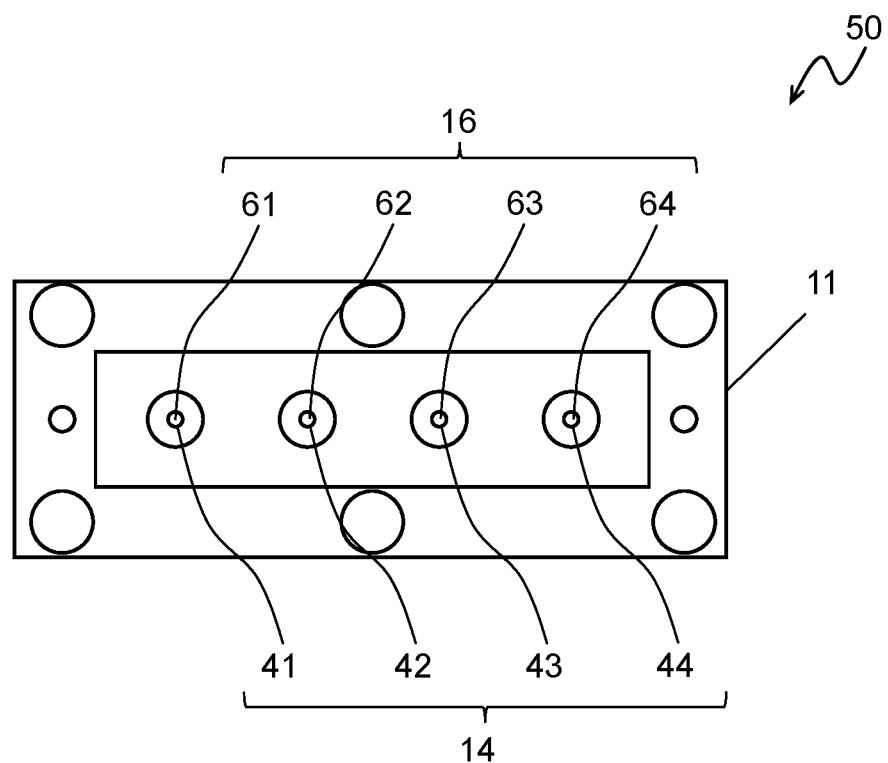
FIG. 10 is a top view of an electrochemical measuring device in accordance with a second exemplary embodiment.

FIG. 10 is a top view of electrochemical measuring device 50 in accordance with this exemplary embodiment. This exemplary embodiment is different from the first exemplary embodiment in that this exemplary embodiment provides a measuring method for measuring a plurality of biological samples 101 provided in electrochemical measuring device 50 in parallel.

Electrochemical measuring device 50 includes a plurality of wells 41, 42, 43, and 44 in reservoir portion 13. In this exemplary embodiment, well 41, 42, 43, and 44 are collectively referred to as well 14. The number of wells 14 is two or more and six or less. Electrode chip 12 is disposed under each well 14. Working electrode 61 is provided at well 41. Working electrode 62 is provided at well 42. Working electrode 63 is provided at well 43. Working electrode 64 is provided at well 44. In this exemplary embodiment, working electrodes 61, 62, 63, and 64 are collectively referred to as working electrode 16.

One each of biological samples 101 is disposed in each region 15 in well 14.

An operation method of electrochemical measuring device 50 in accordance with this exemplary embodiment is the same as in the first exemplary embodiment.

Figure 11:
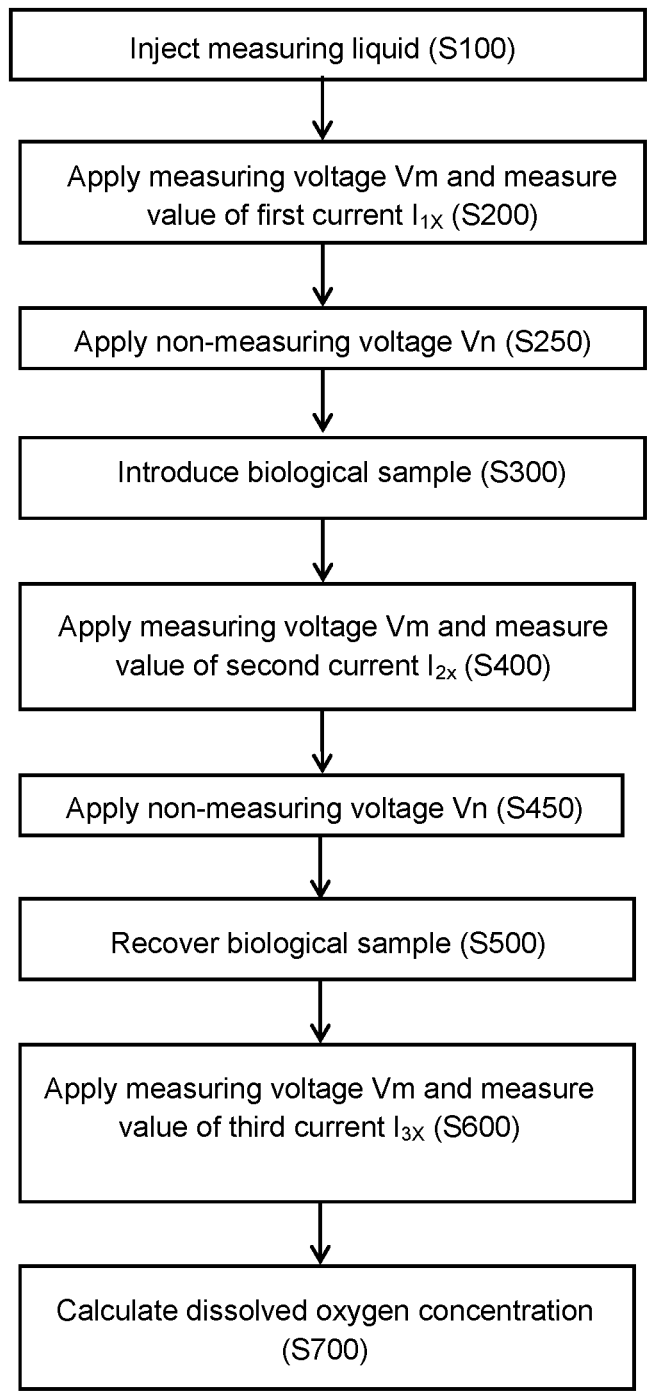
FIG. 11 is a flowchart showing an electrochemical measuring method in accordance with the second exemplary embodiment.

FIG. 11 is a flowchart showing an electrochemical measuring method in accordance with this exemplary embodiment. Hereinafter, a method for measuring activity states of a plurality of biological samples 101 in accordance with the second exemplary embodiment is described.

The electrochemical measuring method in accordance with this exemplary embodiment includes a step of injecting measuring liquid 102 into container 11 (S100); a step of applying measuring voltage Vm to each of working electrodes 16 and measuring a value of first current $I_{1X}$ in a blank state before biological sample 101 is introduced in each well 14 (S200); a step of applying non-measuring voltage Vn to each of working electrodes 16 (S250); a step of introducing one each of a plurality of biological samples 101 into each well 14 (S300); a step of applying measuring voltage Vm to each of working electrodes 16 and measuring a value of second current $I_{2X}$ after biological sample 101 is introduced in each well 14 (S400); a step of applying non-measuring voltage Vn to each of working electrodes 16 (S450); a step of recovering biological sample 101 from each well 14 (S500); a step of applying measuring voltage Vm to each of working electrodes 16, and measuring a value of third current $I_{3X}$ in a blank state after biological sample 101 is recovered in each well 14 (S600); a step of calculating a concentration of the dissolved oxygen (amount of dissolved oxygen) as a substance concentration in measuring liquid 102 of each well 14 from the measured current values $I_{1X}$, $I_{2X}$, and $I_{3X}$ (S700). From a change of the dissolved oxygen concentration, the activity of biological sample 101 is measured.

Figure 12:
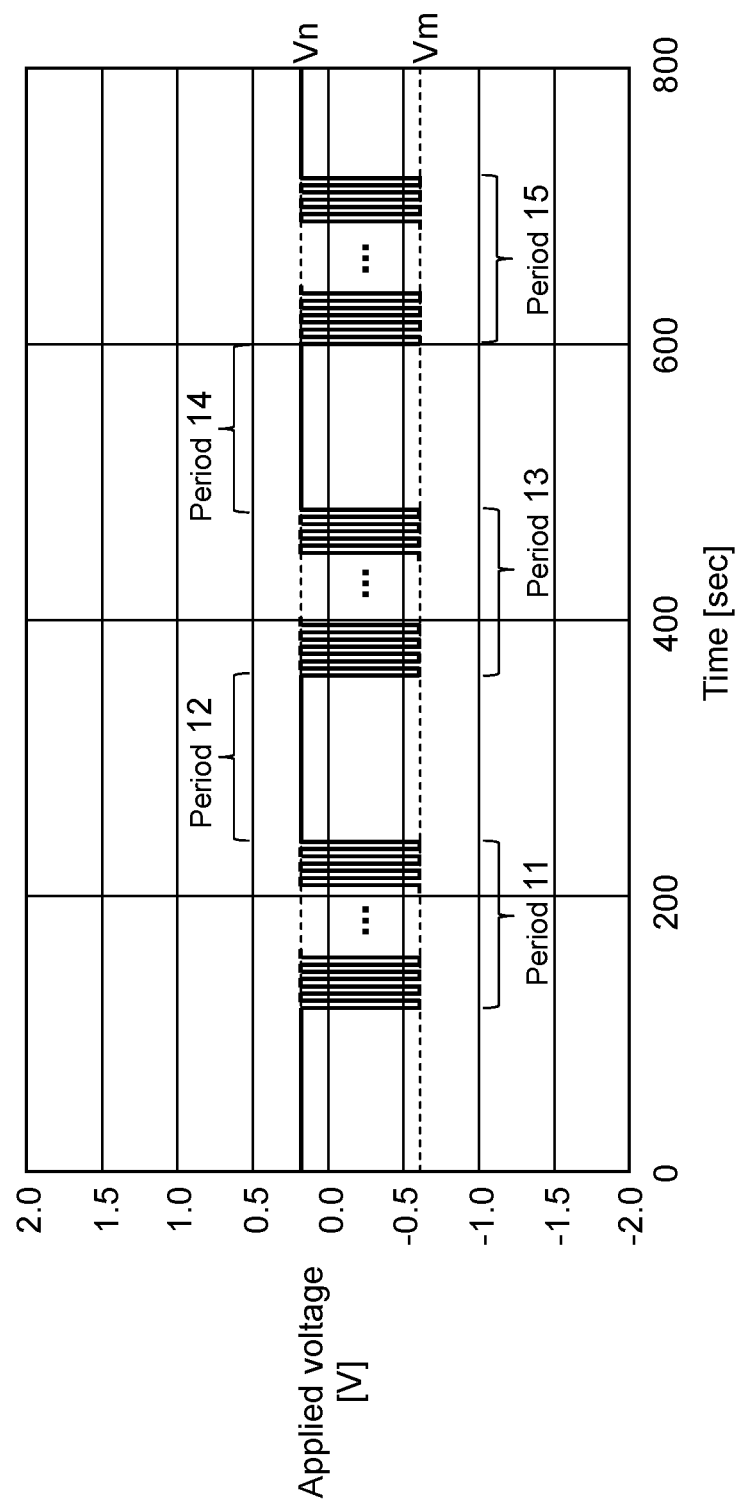
FIG. 12 is a graph showing a voltage application protocol in accordance with the second exemplary embodiment.
Figure 13:
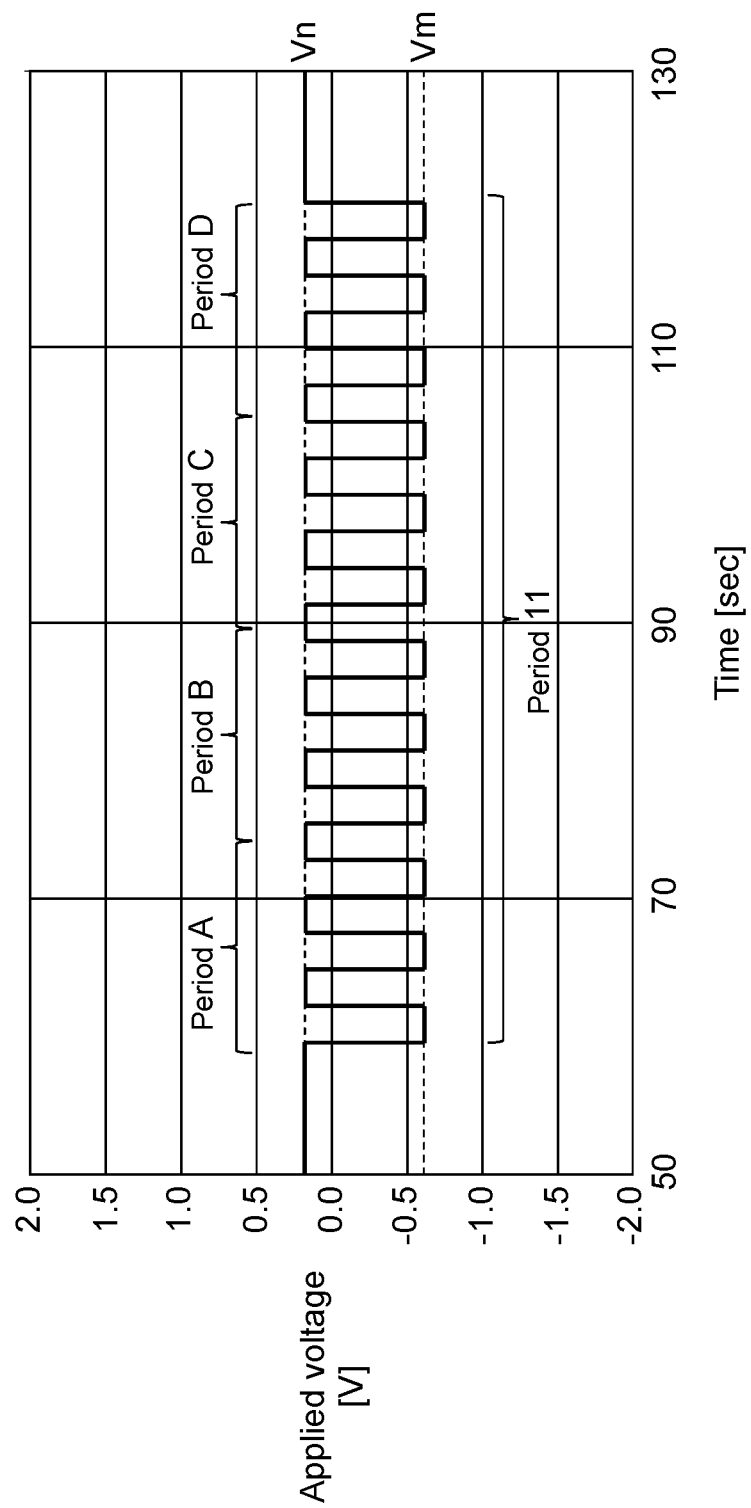
FIG. 13 is a graph showing an example of period 11 of the voltage application protocol in accordance with the second exemplary embodiment.

FIG. 12 is a graph showing a voltage application protocol in accordance with this exemplary embodiment. FIG. 13 is a graph showing an enlarged period 11 in FIG. 12.

In step S100, measuring liquid 102 is injected into container 11.

In step S200, measuring voltage Vm is sequentially applied to working electrodes 16 disposed in each of a plurality of wells 14, and the value of first current $I_{1X}$ before biological sample 101 is introduced is measured in working electrodes 16 of a plurality of wells 14. Herein, the value of first current $I_{1X}$ shows each current value in each well 14. Measuring voltage Vm is applied to working electrodes 16 in period 11.

The voltage application protocol shown in FIG. 13 measures the value of first current $I_{1X}$ flowing in working electrode 16 of each well once in period 11.

Hereinafter, a method for applying a voltage is specifically described.

Period 11 includes periods A, B, C, and D.

In period A, measuring voltage Vm is applied to working electrode 61 disposed in one well 41 of the plurality of wells 14. Thus, a value of first current $I_{11}$ flowing in working electrode 61 in well 41.

In period B, measuring voltage Vm is applied to working electrode 62 disposed in one well 42 of the plurality of wells 14. Thus, a value of first current $I_{12}$ flowing in working electrode 62 in well 42.

In period C, measuring voltage Vm is applied to working electrode 63 disposed in one well 43 of the plurality of wells 14. Thus, a value of first current $I_{13}$ flowing in working electrode 63 in well 43.

In period D, measuring voltage Vm is applied to working electrode 64 disposed in one well 44 of the plurality of wells 14. Thus, a value of first current $I_{14}$ flowing in working electrode 64 in well 44.

In each period, measuring voltage Vm applied to working electrode 16 is a pulse-like voltage. Note here that in each period, measuring voltage Vm applied to working electrode 16 may be a constant voltage.

Thus, by sequentially switching working electrodes 16 to which measuring voltage Vm is applied, the value of first current $I_{1X}$ flowing in each working electrode can be measured sequentially.

In step S250, non-measuring voltage Vn is applied to each of working electrodes 16. Then, in step S300, each one of a plurality of biological samples 101 is introduced into each of the plurality of wells 14. Non-measuring voltage Vn is applied to working electrode 16 in period 12.

In step S400, measuring voltage Vm is applied sequentially to each working electrode 16 disposed in each of the plurality of wells 14, a value of second current $I_{2X}$ after biological sample 101 is introduced is measured in working electrode 16 of each of a plurality of wells 14. Herein, a value of second current $I_{2X}$ shows each current value in each well 14. Measuring voltage Vm is applied to working electrodes 16 in period 13.

In step S400, measuring voltage Vm is applied to working electrode 16 by the same voltage applying method in step S200. Thus, a value of second current $I_{2X}$ can be measured.

In step S450, non-measuring voltage Vn is applied to each of working electrodes 16. Then, in step S500, a plurality of biological samples 101 is recovered. Non-measuring voltage Vn is applied to working electrode 16 in period 14.

In step S600, measuring voltage Vm is applied sequentially to working electrodes 16 respectively disposed in the plurality of wells 14, and a value of third current $I_{3X}$ after biological sample 101 is recovered in working electrode 16 of each of well 14. Herein, the value of third current $I_{3X}$ shows each current value in each well 14. Measuring voltage Vm is applied to working electrodes 16 in period 15.

In step S600, measuring voltage Vm is applied to working electrodes 16 by the same voltage applying method as in step S200. Thus, the value of third current $I_{3X}$ can be measured.

In step S700, the dissolved oxygen concentration (amount of dissolved oxygen) in measuring liquid 102 of each well 14 is calculated from the measured current values $I_{1X}$, $I_{2X}$, and $I_{3X}$.

Figure 14:
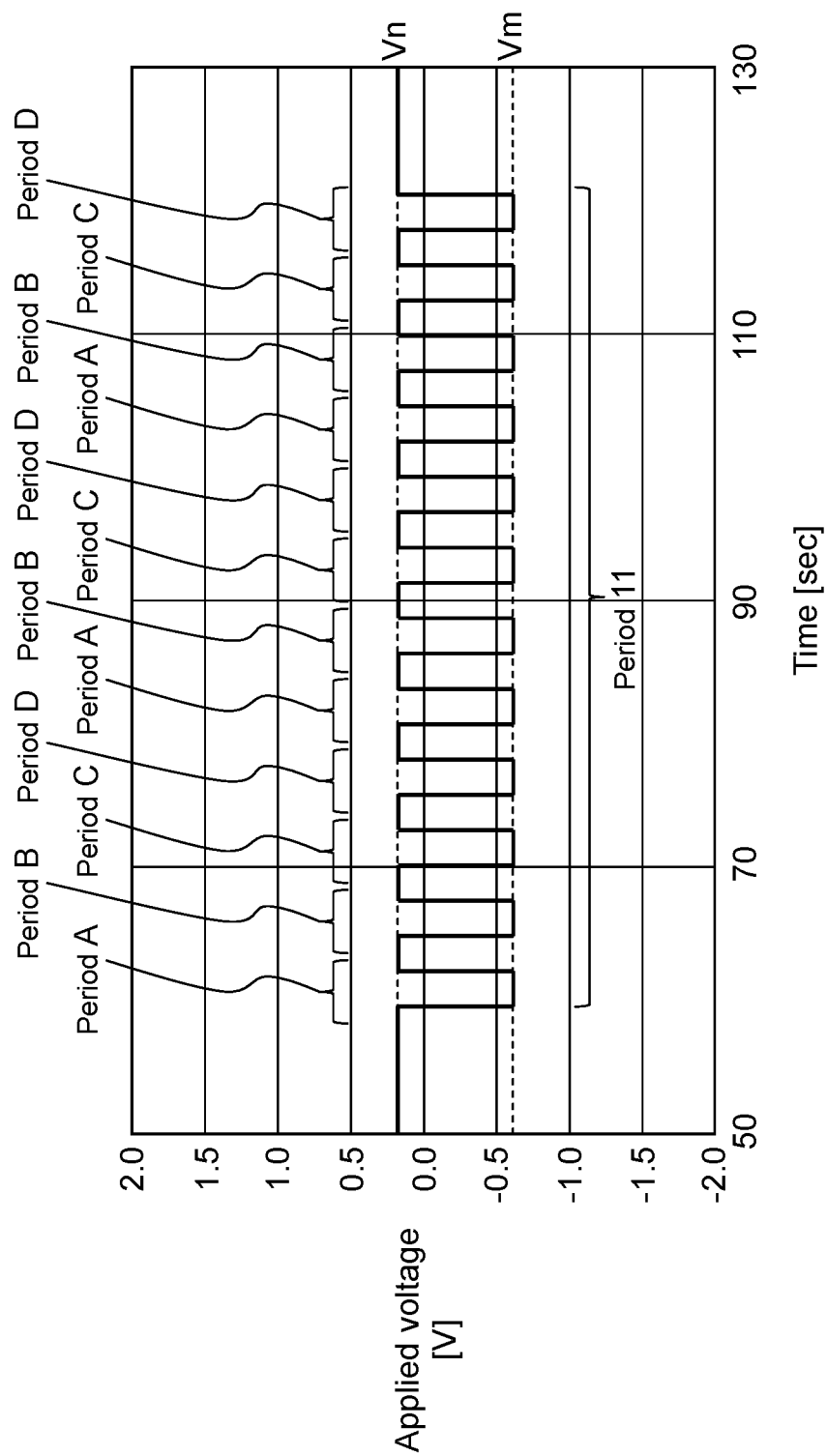
FIG. 14 is a graph showing another example of period 11 of the voltage application protocol in accordance with the second exemplary embodiment.

FIG. 14 is a graph showing another voltage application protocol in accordance with this exemplary embodiment.

As shown in FIG. 14, in steps S200, S400 and S600, an operation of sequentially applying measuring voltage Vm to working electrodes 16 respectively disposed in the plurality of wells 14 is repeated a plurality of times. Thus, the value of first current $I_{1X}$, a value of second current $I_{2X}$ and a value of third current $I_{3X}$ are measured. That is to say, in measurement of current value in each step, the periods A to D are repeated a plurality of times.

Control unit 34 measures voltage Vm to be applied to working electrode 16 of each well 14 by switching working electrodes 16 for each pulse. In this way, by switching of wells for each pulse, time interval for measurement of well 14 in blank measurement and that in measurement of activity of biological sample in step S400, step S200, and S600 can be substantially the same. Note here that measuring voltage Vm to be applied to working electrode 16 in each period of one operation is not limited to one pulse, and may be a plurality of pulse waveforms.

The total number of pulses is a multiple of the number of fertilized eggs to be measured.

Note here that it is preferable that the number of pulses and pulse width of measuring voltage Vm to be applied to working electrode 61 are equal to the number of pulses and a pulse width of measuring voltage Vm to be applied to the other working electrodes 62, 63, and 64.

As mentioned above, the electrochemical measuring method and the electrochemical measuring apparatus in accordance with one or a plurality of embodiments are described based on the exemplary embodiments. However, the present disclosure is not limited to this exemplary embodiments. For example, the electrochemical measuring method may be a program to be executed.

Various modifications to the present embodiment that can be conceived by a person skilled in the art, and forms configured by combining constituent elements in different embodiments without departing from the teachings of the present disclosure may be included in the scope of one or a plurality of embodiments.

The electrochemical measuring method and the electrochemical measuring apparatus in accordance with the present disclosure can suppress a current noise generated according to introduction or recovery of a biological sample.

INDUSTRIAL APPLICABILITY

An electrochemical measuring method and an electrochemical measuring apparatus of the present disclosure are useful for measurement of an activity state of substances of biological origin, such as a fertilized egg and a cell.

REFERENCE MARKS IN THE DRAWINGS 10, 50 electrochemical measuring device
11 container
11a upper container
11b lower container
12 electrode chip
13 reservoir portion
14, 41, 42, 43, 44 well
15 region
16, 61, 62, 63, 64 working electrode
17 connection terminal
18 sealing member
23 reference electrode
24 counter electrode 30 electrochemical measuring apparatus
31 stage
32 mounting portion
33 terminal
34 control unit
35 cover
36 measurement unit
37 operation unit
53 through hole
101 biological sample
102 measuring liquid

The invention claimed is:

1. A method for analyzing a biological sample, using an electrochemical measuring device including a well and a working electrode provided at the well, wherein a measuring liquid is filled into the well such that the measuring liquid is in contact with the working electrode, the method comprising steps of:
applying, without the biological sample being introduced in the well, a measuring voltage to the working electrode, and measuring a value of a first current flowing in the working electrode;
then applying, without the biological sample being introduced in the well, a non-measuring voltage different from the measuring voltage to the working electrode;
then, while applying the non-measuring voltage, introducing the biological sample into the well;
then, with the biological sample being introduced in the well, applying the measuring voltage to the working electrode, and measuring a value of a second current flowing in the working electrode; and
measuring an activity of the biological sample based on the value of the first current and the value of the second current,
wherein the non-measuring voltage is a voltage such that a value of a current flowing through the working electrode when the non-measuring voltage is applied to the working electrode is smaller than the value of the first current,
the measuring voltage causes a reduction current to flow in the working electrode upon the measuring voltage being applied to the working electrode, and
the non-measuring voltage causes the reduction current not to flow in the working electrode upon the non-measuring voltage being applied to the working electrode.

2. The method of claim 1, further comprising steps, after the step of measuring the value of the second current, of:
applying, with the biological sample being introduced in the well, the non-measuring voltage to the working electrode;
then, while applying the non-measuring voltage, recovering the biological sample; and
then, without the biological sample being introduced in the well, applying the measuring voltage to the working electrode, and measuring a value of a third current.

3. The method of claim 2, wherein the step of measuring an activity includes steps of:
calculating a substance concentration in the measuring liquid in each of the steps of measuring the value of the first current, measuring the value of the second current, and measuring the value of the third current, based on the value of the first current, the value of the second current, and the value of the third current, and
measuring an activity of the biological sample from the substance concentration.

4. The method of claim 3, wherein in the step of calculating the substance concentration, the value of the second current is corrected using the value of the first current and the value of the third current.

5. The method of claim 3, wherein the step of measuring the activity of the biological sample from the substance concentration includes a step of measuring the activity of the biological sample from a change amount of the substance concentration.

6. The method of claim 1, wherein the non-measuring voltage is an open-circuit voltage of an electrochemical measuring apparatus connected to the electrochemical measuring device.

7. The method of claim 1, wherein the measuring voltage applied to the working electrode has a pulse-like waveform.

8. The method of claim 1, further comprising a step of applying the measuring voltage to the working electrode after the measuring liquid is injected and before the step of measuring the value of first current.

9. The method of claim 1, wherein the step of measuring the activity of the biological sample includes steps of:
calculating a substance concentration in the measuring liquid in each of the steps of measuring the value of the first current and measuring the value of the second current, based on the value of the first current and the value of the second current, and
measuring the activity of the biological sample from the substance concentration.

10. The method of claim 9, wherein the step of measuring the activity of the biological sample from the substance concentration includes a step of measuring the activity of the biological sample from a change amount of the substance concentration.

11. A method for analyzing a plurality of biological samples, using an electrochemical measuring device including a plurality of wells and a plurality of working electrodes provided at the plurality of wells, respectively, wherein a measuring liquid is filled into the plurality of wells such that the measuring liquid is in contact with the plurality of working electrodes, the method comprising steps of:
without the plurality of biological samples being introduced in the plurality of wells, respectively, sequentially applying a measuring voltage to the plurality of working electrodes, and measuring a plurality of values of first currents flowing in the plurality of working electrodes, respectively;
then, without the plurality of biological samples being introduced in the plurality of wells, respectively, applying a non-measuring voltage different from the measuring voltage to each of the plurality of working electrodes and while applying the non-measuring voltage, introducing one each of the plurality of biological samples into each of the plurality of wells;
then, with the plurality of biological samples being introduced in the plurality of wells, respectively, sequentially applying the measuring voltage to each of the plurality of working electrodes, and measuring a plurality of values of second currents flowing in the plurality of working electrodes, respectively, and
measuring an activity of the plurality of biological samples based on the plurality of values of the first currents and the plurality of values of the second currents,
wherein the non-measuring voltage is a voltage such that values of currents flowing through the plurality of working electrodes when the non-measuring voltage is applied to the each of the plurality of working electrodes are smaller than the values of the first currents, the measuring voltage causes a reduction current to flow in the each of the plurality of working electrodes upon the measuring voltage being applied to the each of the plurality of working electrodes, and the non-measuring voltage causes the reduction current not to flow in the each of the plurality of working electrodes upon the non-measuring voltage being applied to the each of the plurality of working electrodes.

12. The method of claim 11, further comprising the steps, after the step of measuring the plurality of values of the second currents, of:

applying, with the plurality of biological samples being introduced in the plurality of wells, respectively, the non-measuring voltage to each of the plurality of working electrodes;

then, while applying the non-measuring voltage to each of the plurality of working electrodes, recovering the plurality of biological samples; and then, without the plurality of biological samples being introduced in the plurality of wells, respectively, sequentially applying the measuring voltage to the plurality of working electrodes and measuring a plurality of values of third currents flowing in each of the plurality of working electrodes, respectively.

13. The method of claim 12, wherein in each of the steps of measuring the plurality of values of the first currents, measuring the plurality of values of the second currents, and measuring the plurality of values of the third currents, the measuring voltage is applied once to each of the plurality of working electrodes disposed in each of the plurality of wells.

14. The method of claim 13, wherein the measuring voltage to be applied once to the plurality of working electrodes is a pulse-like measuring voltage.

15. The method of claim 12, wherein in each of the steps of measuring the plurality of values of the first currents, measuring the plurality of values of the second currents, and measuring the plurality of values of the third currents, an operation of sequentially applying the measuring voltage to each of the plurality of working electrodes is repeated a plurality of times.

16. The method of claim 11, wherein the non-measuring voltage is a voltage by which the plurality of values of the second currents become smaller than the plurality of values of the first currents.

* * * * *